(12) United States Patent
Korte

(10) Patent No.: US 8,696,652 B2
(45) Date of Patent: Apr. 15, 2014

(54) LIGHT THERAPY DEVICE AND SYSTEM FOR PREPARING AND APPLYING A THERAPEUTICALLY EFFECTIVE LIQUID

(76) Inventor: Andreas Korte, Neuhausen am Rheinfall (CH)

( * ) Notice: Subject to any disclaimer, the term of this patent is extended or adjusted under 35 U.S.C. 154(b) by 111 days.

(21) Appl. No.: 13/195,205

(22) Filed: Aug. 1, 2011

(65) Prior Publication Data

US 2012/0029603 A1 Feb. 2, 2012

(30) Foreign Application Priority Data

Aug. 2, 2010 (DE) .......................... 10 2010 033 046

(51) Int. Cl.
*A61B 17/00* (2006.01)

(52) U.S. Cl.
USPC ........ 606/1; 607/88; 607/89; 607/90; 607/91; 607/92; 607/93; 607/94; 607/95

(58) Field of Classification Search
USPC .......................................... 606/1; 607/88–95
See application file for complete search history.

(56) References Cited

U.S. PATENT DOCUMENTS

| | | | | |
|---|---|---|---|---|
| 5,233,414 A | * | 8/1993 | Kojima | .......................... 358/518 |
| 6,082,865 A | * | 7/2000 | Yamazaki | ..................... 353/122 |
| 6,149,672 A | | 11/2000 | Ruschke | |
| 2004/0208007 A1 | * | 10/2004 | Munari | ......................... 362/293 |

FOREIGN PATENT DOCUMENTS

| | | |
|---|---|---|
| DE | 19742299 A1 | 4/1999 |
| DE | 10104762 A1 | 5/2002 |
| DE | 20202230 U1 | 5/2002 |

* cited by examiner

*Primary Examiner* — Aaron Roane
(74) *Attorney, Agent, or Firm* — Bachman & LaPointe, P.C.

(57) ABSTRACT

A light therapy device for applying an image produced from a therapeutically effective aqueous liquid, is provided. The device includes a slide, prepared by Kirlian and/or corona discharge photography, of a sample of an aqueous liquid removed from a liquid-retaining body and mixed with ethanol, and a projection device with a light device which emits visible light and is designed to project the slide onto an object, in particular a living being, in such a way that a sample of the liquid contained in a container which is permeable to and can be irradiated by the visible light is arranged in a light path between a unit, which holds the slide, of the projection device and the object.

11 Claims, 2 Drawing Sheets

LIGHT THERAPY DEVICE AND SYSTEM FOR PREPARING AND APPLYING A THERAPEUTICALLY EFFECTIVE LIQUID

BACKGROUND

The present invention relates to a light therapy device and a system for preparing a therapeutically effective liquid which subsequently acts as a basis for the application of an image produced therefrom.

'Light therapy' has been known from the prior art for many years. Illumination and radiation devices designed for this purpose are used to exert a therapeutic effect on living beings, in particular humans, this effect typically being expressed in improved well-being although further effects of colour and/or light therapy are also known which concern, for example, stimulation of the immune system, the suitability for the treatment of psychosomatic disorders also being documented and recent medical publications even documenting therapeutic effects on humans in terms of behaviour.

In terms of technical implementation numerous technologies for the application of suitably therapeutically modulated (for example chromatically coloured) light rays are known. Reference is made, in a merely exemplary manner, to document DE 202 02 230 U1, which describes a use in a bathing or sanitary context; in this case light emitters (which can be suitably modulated) are assigned to walls of a bathtub, radiate through the filling water onto a person located in the tub and thus trigger the intended therapeutic improvement in well-being. Therapists report that the liquid effect contributes positively to the therapeutic effect of light therapy implemented in such a conventional manner, such systems also recently attracting a high level of public attention, in particular for private use, too.

However, a conventional approach of this type is limited owing to its constructional possibilities and the required technical cost, and the known sanitary context typically allows for limited possible variations.

SUMMARY OF THE INVENTION

The problem on which the present invention is based is therefore to create a light therapy device which offers alternative ways to generate therapeutically effective radiation, in particular which increases the well-being of living beings, can be implemented at low cost and is improved in terms of the desired therapeutic effect.

The problem is solved by the light therapy device having the features of the main claim and the system having the features of independent claim 6. Advantageous developments of the invention are described in the dependent claims. In addition, within the scope of the present invention a method for producing an image which can be used for the light therapy device, as is discernible from the entire present disclosure, is claimed as belonging to the invention.

The light therapy device according to the invention advantageously makes it possible to produce an image by means of Kirlian photography from a sample of an aqueous liquid which is removed from a liquid-retaining body (preferably formed from a crystal) and mixed with ethanol, and to project the image of this liquid (more specifically: the imaging formed on the slide as a reaction to the Kirlian exposure technique) onto a living being with the aid of the projection device according to the invention.

It has therefore surprisingly been found in accordance with the invention that therapeutically effective results, in particular effects improving a subjective well-being of a human can be achieved, the specific image representation of the projected slide obtained from the Kirlian photography in conjunction with the irradiated liquid sample which is arranged in the light path being the cause for this effect.

Within the scope of the invention the light therapy device thus advantageously provides, at low technical cost, an alternative to traditional colour therapy and illumination systems, the practical testing of the present invention revealing, further to consistently positive assertions regarding the therapeutic effect on the well-being of the individual irradiated in this manner, indications of positive effects which influence behaviour, in particular with regard to decreasing tendency towards violence, alleviation of ADD behavioural patterns (ADD=attention deficit disorder) or positive stimulant effect on the human immune system of the individual irradiated in this manner.

Within the scope of the present invention "Kirlian photography" is understood to mean photography carried out using techniques of "corona discharge photography" (also known as high-frequency high-voltage photography), with which glow or corona discharges (which can be traced back to the discoverer: Kirlian) are visualised. When implemented in practice the object to be detected photographically, in this case a sample of the aqueous liquid mixed with ethanol, is brought, in an otherwise known manner, into an electric field together with the film material, which is still unexposed at this point, in such a way that the aqueous liquid, relative to a counter electrode which, for example, is made of metal, forms a corona discharge under high voltage (typical value 20 kV) which then exposes the film material and is developed to form a slide.

In particular when using standardised, otherwise known photo materials, for example photo material in established small image format or medium format, cost-effective material is available which makes it possible to produce the slide in the manner described. This can also be used, with the aid of the use of established slide projectors, to form the projection device according to the invention, wherein when implemented in practice the slide prepared in the manner described is projected onto the target object, for example the individual to be treated, a sample (from which the slide was prepared) of said liquid contained in the container through which light can pass being provided in the light path either manually or by means of mechanical mounting, and the projector used to form the projection device comprising a projection light means in a particularly suitable manner, the emission spectrum of said projection light means being close to that of sunlight.

A projection system thus formed can therefore have an advantageous and unexpected well-being-promoting and health-promoting therapeutic effect on an irradiated person in the manner described above.

Within the scope of the present invention a system for preparing the therapeutically effective liquid is also claimed, in addition to the light therapy device discussed above, and can subsequently be used in the manner described above for the preparation of the slide formed by means of Kirlian photography, and for the sample to be irradiated which can be placed in the light path. Within the scope of the system according to the invention a liquid-retaining body is provided for this purpose and comprises a cavity which is defined by a transparent crystal outer layer. In a preferred embodiment this body is a naturally occurring mineral geode, namely a quartz body which comprises, in the manner of a shell, an outer wall as a crystal outer layer which is formed by the transparent quartz material and is thus transparent.

In accordance with the invention this retaining body is advantageously adapted to retain an aqueous fluid, typically with a volume between approximately 5 and 200 ml, natural spring water further preferably being advantageous for filling. The liquid receiving body according to the invention is designed in such a way, in particular can be manually handled, that it can be used in a daylight environment in the open air, it being possible for rays of daylight or incident light reflected by objects to pass through the crystal outer layer and reach the aqueous liquid arranged in the cavity.

A liquid of this type is adapted for subsequent further treatment, for example for mixing with ethanol (for example a mixing ratio between 30% and 70% ethanol volume fraction is advantageous), and the mixture thus prepared can then be used in the manner described above to prepare the slide, and for further use in the irradiation and projection system.

As a result, the present invention makes it possible, in a surprisingly technically simple manner, to provide a light therapy device and a system which enables light therapy for living beings, in particular humans, which excites the organism in a surprisingly effective manner, stimulates the immune system and self-healing powers and, in addition to having a positive effect on subjective well-being, also has positive effects on behavioural reactions.

BRIEF DESCRIPTION OF THE DRAWINGS

Further advantages, features and details of the invention will emerge from following description of preferred embodiments and from the drawings, in which.

DETAILED DESCRIPTION

Figure 1:
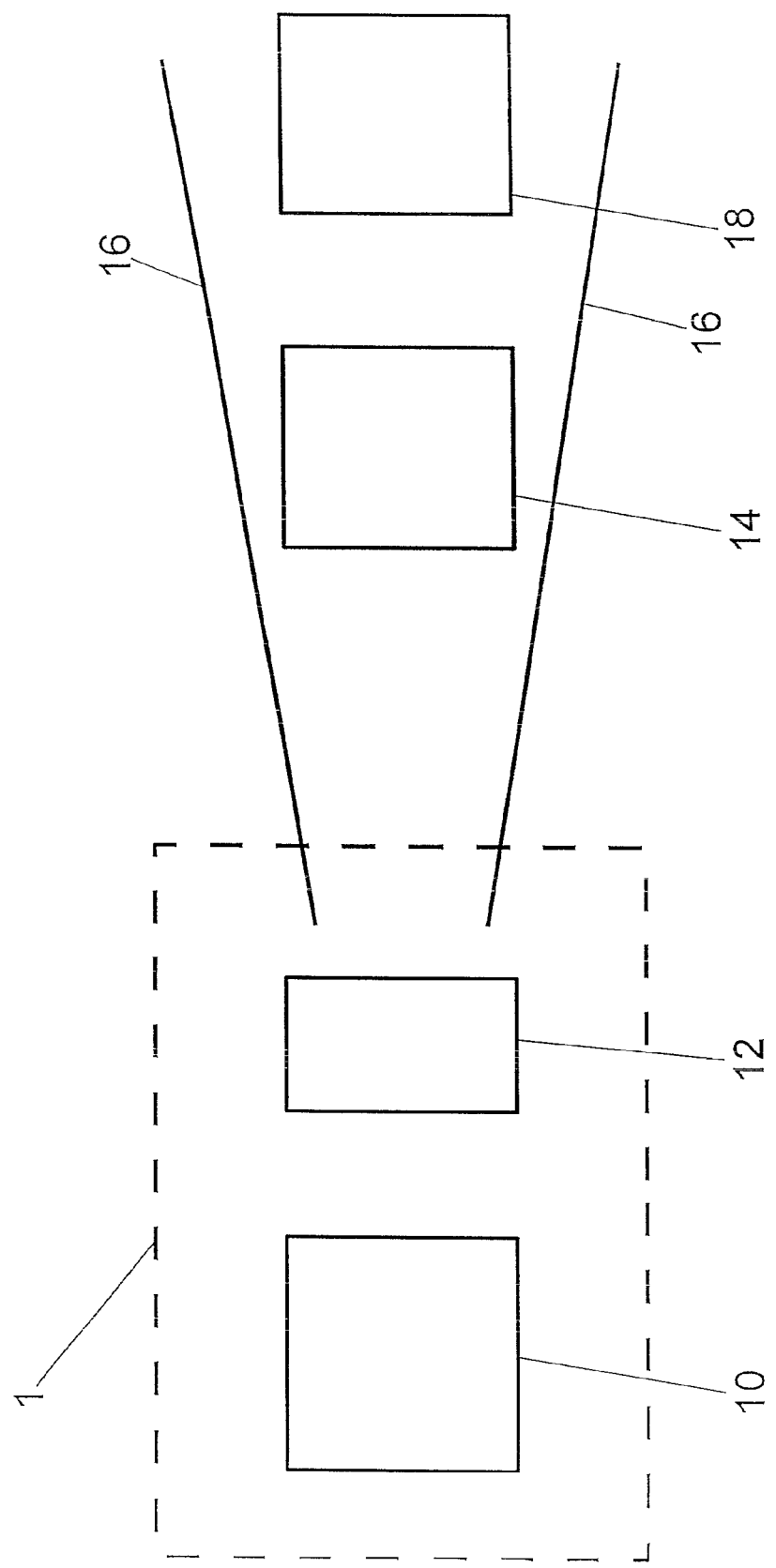
FIG. 1 is a block diagram of a light therapy device according to the invention in accordance with a first, preferred embodiment of the present invention.

A schematically illustrated projection unit 1, typically produced in the form of a conventional commercial slide projector for small image format (24×36 mm edge length of an irradiated slide), comprises a schematically illustrated light means 10 as a projector lamp, with which an image carrier 12 for the slides to be projected is associated in an otherwise known manner. In the operating state this arrangement generates a light path, illustrated schematically by reference numeral 16, which is directed onto an object 18 which, within the scope of the aim of the light therapy in accordance with the invention, may be a living organism, for example a patient. A sample 14 in the form of a tubular glass vessel through which the light of the light path 16 can pass and in which a predetermined amount, for example 5 mm, of a therapeutically effective aqueous liquid is contained reaches into the light path 16 and is supported on a sample carrier (not shown in greater detail, this support also possibly being provided by way of manual handling by an operator who is not shown in this instance).

In a manner not shown in greater detail in FIG. 1 the slide carrier 12 carries a slide, prepared by means of the above-described Kirlian photography, of a sample of the same liquid which is contained in the container 14. Spring water from a mineral geode which was subjected to natural sunlight over a period in the range between 10 and 300 min was mixed with ethanol, after being removed from the geode, before the Kirlian photography was carried out, the amount of the mixture used for this being selected in such a way that an approximately full frame corona image was produced as a slide.

In FIG. 1 the relative distances between the sample 14 and the projection unit 1, and between the sample 14 and the illuminated object 18 (patient) are not shown in detail; these conform to the respective focal lengths and projection conditions, it being preferred to orient and adjust the respective functional units in such a way that the object 18 is irradiated over at least half of its vertical direction of extension (relative to the light path, i.e. at least half the height of the body, for example) and the sample 14 arranged in the irradiated sample carrier influences associated portions of the light path 16.

Figure 2:
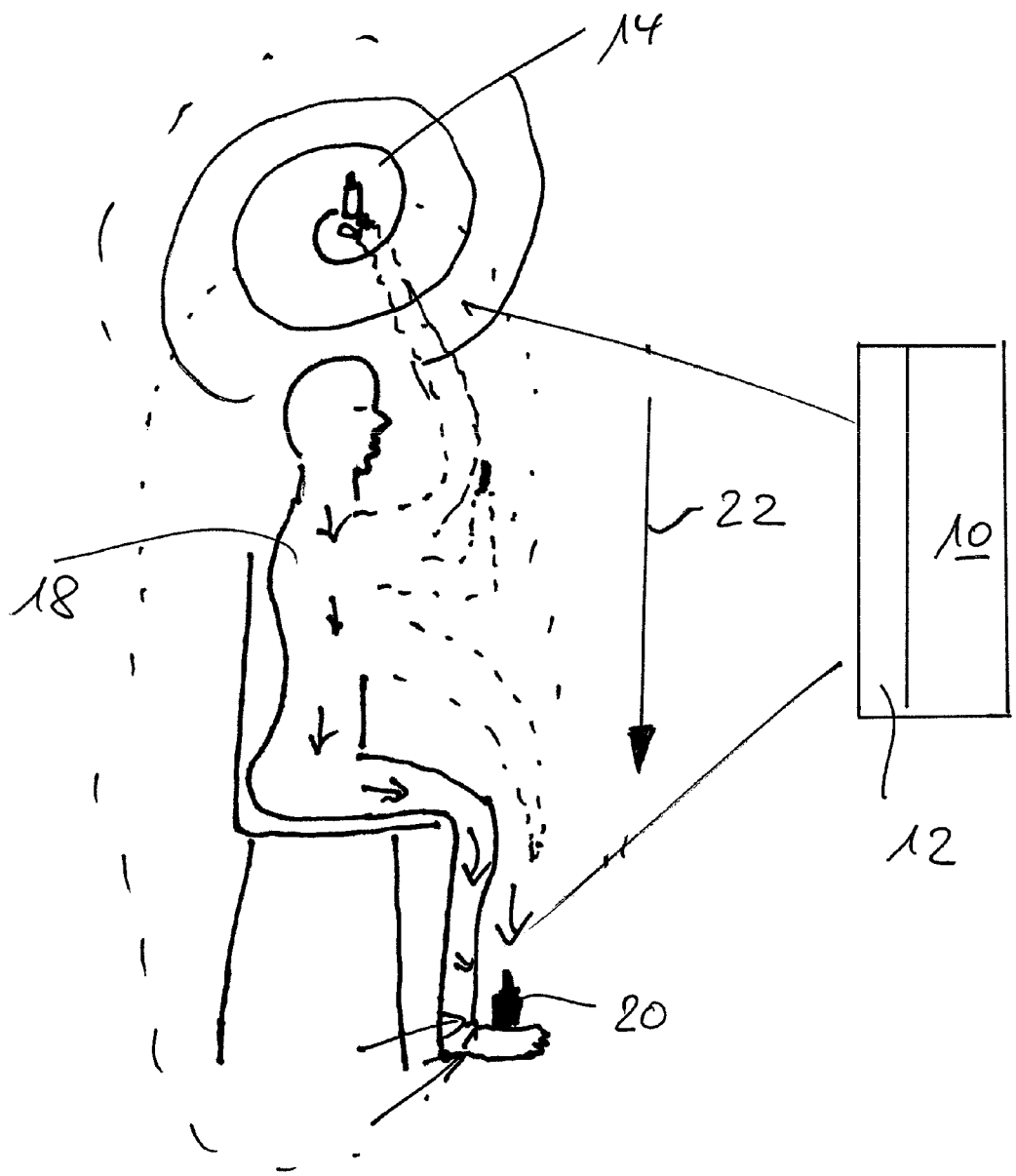
FIG. 2 shows an alternative way of using the light therapy device.

FIG. 2 shows an alternative mode of using the light therapy device of FIG. 1: Projector 10 projects the slide image 12 onto a patient 18, holding the sample vessel 14 above the head (nevertheless within the light path 16). To further stimulate an effective energy flow along path (arrow) 22, patient 18 encloses another vessel 20 with the feet, this vessel 20 to be advantageously filled with an aqueous solution of a therapeutically effective agent, such as the liquid of vessel 14, or, alternatively, a liquid available as T1 Essence by the inventor. This embodiment of the invention has also been found effective without the slide 12 provided in the light path.

The present invention is not limited to the specific embodiments. Rather, there are numerous modifications and variations for designing and constructing the light therapy device illustrated in accordance with a respective therapeutic purpose or therapeutic object. It is also left to the discretion of the person skilled in the art to provide an irradiation period and irradiation intensity which are adapted for a respective therapeutic purpose or object to be illuminated (for example by suitable adjustment of the light intensity of the light means 10).

The invention claimed is:

1. A system for preparing a therapeutically effective aqueous liquid and for applying an image produced from the liquid, said system comprising a light therapy device comprising a slide of a sample of an aqueous liquid mixed with ethanol; said slide being prepared by means of Kirlian and/or corona discharge photography and including an exposed film material; an image carrier for the slide; a projection device for emitting visible light so that said slide being held by said image carrier is projected onto a patient; and a liquid-retaining body permeable to said visible light being placed in a light path created by said projection device, said liquid-retaining body containing said aqueous liquid and being positioned so that said liquid-retaining body and said aqueous liquid therein is irradiated by said visible light, wherein said sample of said aqueous liquid used for said slide is removed from said aqueous liquid in said container and the liquid-retaining body, comprising a cavity defined by a transparent crystal outer layer.

2. The system according to claim 1, wherein the liquid-retaining body is made of a quartz material and comprises a filling volume of the cavity between 5 ml and 200 ml.

3. The system according to claim 2, wherein the liquid retaining body is a mineral geode.

4. The system according to claim 1, wherein the liquid-retaining body can be manually handled and can be held at least by one hand such that light rays can pass through the crystal outer layer and reach said aqueous liquid received in the cavity.

5. The system according to claim 1, wherein the aqueous liquid is spring water and said liquid-receiving body is filled with said spring water and is kept in a daylight environment in open air.

6. A light therapy device comprising:
a slide of a sample of an aqueous liquid mixed with ethanol;

said slide being prepared by means of Kirlian and/or corona discharge photography and including an exposed film material;

an image carrier for the slide;

a projection device for emitting visible light so that said slide being held by said image carrier is projected onto a patient; and a liquid-retaining body permeable to said visible light being placed in a light path created by said projection device, said liquid-retaining body containing said aqueous liquid and being positioned so that said liquid-retaining body and said aqueous liquid therein is irradiated by said visible light, wherein said sample of said aqueous liquid used for said slide is removed from said aqueous liquid in said container.

7. The device according to claim 6, wherein the slide is rectangular with a first and second edge length in a range between 12 mm and 60 mm.

8. The device according to claim 6, wherein a sample volume of the aqueous liquid applied to the film material of the slide is between 0.01 and 10 ml.

9. The device according to claim 6, wherein the projection device comprises a projector which is suitable for slides of at least one of small image format and medium format, which is set up to generate a radiation spectrum corresponding to sunlight.

10. The device according to claim 9, wherein the projection device is a daylight projector.

11. The device according to claim 6, wherein the liquid-retaining body which is irradiated is produced from a glass material, which is tubular, and is positioned in the light path by at least one of manual handling and mechanical mounting.

* * * * *